(12) United States Patent  
Denis

(10) Patent No.: US 9,922,460 B2
(45) Date of Patent: Mar. 20, 2018

(54) STEREOSCOPIC HELMET DISPLAY

(71) Applicant: ILLINOIS TOOL WORKS INC., Glenview, IL (US)

(72) Inventor: Marc Lee Denis, Lena, WI (US)

(73) Assignee: Illinois Tool Works Inc., Glenview, IL (US)

( * ) Notice: Subject to any disclaimer, the term of this patent is extended or adjusted under 35 U.S.C. 154(b) by 324 days.

(21) Appl. No.: 14/532,734

(22) Filed: Nov. 4, 2014

(65) Prior Publication Data

US 2016/0125653 A1 May 5, 2016

(51) Int. Cl.
*H04N 7/18* (2006.01)
*H04N 9/47* (2006.01)
(Continued)

(52) U.S. Cl.
CPC .......... *G06T 19/006* (2013.01); *B23K 9/0956* (2013.01); *B23K 9/173* (2013.01); *B23K 9/322* (2013.01); *G02B 27/017* (2013.01); *G05B 19/409* (2013.01); *G06F 3/012* (2013.01); *G06F 3/167* (2013.01); *G06T 7/0004* (2013.01); *G06T 7/292* (2017.01); *H04N 5/23241* (2013.01);
(Continued)

(58) Field of Classification Search
None
See application file for complete search history.

(56) References Cited

U.S. PATENT DOCUMENTS 2,045,800 A 6/1936 Walther
2,045,802 A 6/1936 Walther
(Continued)

FOREIGN PATENT DOCUMENTS

CA 2762296 6/2013
DE 2442998 3/1976
(Continued)

OTHER PUBLICATIONS

International Search Report from PCT application No. PCT/US2015/059446, dated Jan. 22, 2016, 13 pgs.
(Continued)

*Primary Examiner* — Talha M Nawaz
(74) *Attorney, Agent, or Firm* — McAndrews, Held & Malloy, Ltd.

(57) ABSTRACT

A welding-type system includes a helmet having a first image capture device configured to capture a first set of images of a work area from a first perspective and a second image capture device configured to capture a second set of images of the work area from a second perspective. The helmet also includes an electronic display configured to display the first and second sets of images substantially simultaneously to cause a stereoscopic appearance of the work area via the electronic display. Moreover, the helmet includes an audible command translation unit configured to receive audible commands configured to adjust operation of a power supply configured to supply power for the welding-type system. Furthermore, the welding-type system includes a processing system communicatively coupled to the audible command translation unit and configured to adjust at least one parameter of the power supply based at least in part on the received audible commands.

30 Claims, 5 Drawing Sheets

(51) Int. Cl.
*G06T 19/00* (2011.01)
*H04N 5/247* (2006.01)
*H04N 5/232* (2006.01)
*G06F 3/16* (2006.01)
*G06T 7/00* (2017.01)
*B23K 9/095* (2006.01)
*G06F 3/01* (2006.01)
*G02B 27/01* (2006.01)
*H04N 13/04* (2006.01)
*B23K 9/32* (2006.01)
*G05B 19/409* (2006.01)
*B23K 9/173* (2006.01)
*G06T 7/292* (2017.01)
*A42B 3/04* (2006.01)
*A61F 9/06* (2006.01)

(52) U.S. Cl.
CPC ......... *H04N 5/247* (2013.01); *H04N 13/0429* (2013.01); *H04N 13/0486* (2013.01); *H04N 13/0497* (2013.01); *A42B 3/042* (2013.01); *A61F 9/06* (2013.01); *G05B 2219/35487* (2013.01); *G05B 2219/45135* (2013.01); *G06T 2200/04* (2013.01); *G06T 2207/30108* (2013.01)

(56) References Cited

U.S. PATENT DOCUMENTS

| | | |
|---|---|---|
| 2,351,910 A | 6/1944 | Blankenbuehler |
| 3,943,573 A | 3/1976 | Budmiger |
| 4,039,254 A | 8/1977 | Harsch |
| 4,101,979 A | 7/1978 | Tarrone |
| 4,124,944 A | 11/1978 | Blair |
| 4,237,557 A | 12/1980 | Gordon |
| 4,293,757 A | 10/1981 | Niemi |
| 4,555,614 A | 11/1985 | Morris |
| 4,559,555 A | 12/1985 | Schoolman |
| 4,620,322 A | 11/1986 | Eggenschwiler |
| 4,641,292 A | 2/1987 | Tunnell |
| 4,677,277 A | 6/1987 | Cook |
| 4,679,255 A | 7/1987 | Kuhlman |
| 4,716,273 A | 12/1987 | Paton |
| 4,721,947 A | 1/1988 | Brown |
| 4,863,244 A | 9/1989 | Fuerthbauer |
| 5,189,735 A | 3/1993 | Corona |
| 5,248,880 A | 9/1993 | Fergason |
| 5,317,643 A | 5/1994 | Patricelli |
| 5,444,232 A | 8/1995 | Gunz |
| 5,533,206 A | 7/1996 | Petrie |
| 5,644,324 A | 7/1997 | Maguire |
| 5,708,460 A | 1/1998 | Young |
| 5,825,441 A | 10/1998 | Hornell |
| 5,845,053 A | 12/1998 | Watanabe |
| 5,877,825 A | 3/1999 | Kotler |
| 5,949,388 A | 9/1999 | Atsumi |
| 6,067,129 A | 5/2000 | Fergason |
| 6,070,264 A | 6/2000 | Hamilton |
| 6,078,021 A | 6/2000 | Chang |
| 6,242,711 B1 * | 6/2001 | Cooper ................. A61F 9/06 219/130.01 |
| 6,456,261 B1 | 9/2002 | Zhang |
| 6,552,316 B1 | 4/2003 | Bae |
| 6,614,409 B1 | 9/2003 | Bae |
| 6,710,298 B2 | 3/2004 | Eriksson |
| 6,734,393 B1 | 5/2004 | Friedl |
| 6,881,939 B1 | 4/2005 | Hamilton |
| 6,941,577 B2 | 9/2005 | Ackermann |
| 7,150,047 B2 | 12/2006 | Fergason |
| 7,161,135 B2 | 1/2007 | Fergason |
| 7,209,039 B2 | 4/2007 | Krebs |
| 7,212,300 B2 | 5/2007 | Comer |
| 7,265,746 B2 | 9/2007 | Knowles |
| 7,271,894 B2 | 9/2007 | Devitt |
| 7,298,535 B2 | 11/2007 | Kuutti |
| 7,342,210 B2 | 3/2008 | Fergason |
| 7,383,654 B2 | 6/2008 | Olivier |
| 7,402,786 B2 | 7/2008 | Schofield |
| 7,411,154 B2 | 8/2008 | Fosbinder |
| 7,501,613 B2 | 3/2009 | Fergason |
| 7,534,005 B1 | 5/2009 | Buckman |
| 7,550,698 B2 | 6/2009 | Fergason |
| 7,683,290 B2 | 3/2010 | Daniel |
| 7,926,118 B2 | 4/2011 | Becker |
| 8,009,229 B1 | 8/2011 | Peterson |
| 8,747,116 B2 | 6/2014 | Zboray |
| 8,834,168 B2 | 9/2014 | Peters |
| 8,851,896 B2 | 10/2014 | Wallace |
| 8,911,237 B2 | 12/2014 | Postlethwaite |
| 8,915,740 B2 | 12/2014 | Zboray |
| 2002/0124271 A1 | 9/2002 | Herrmann |
| 2003/0001950 A1 * | 1/2003 | Eriksson ................... A61F 9/06 348/61 |
| 2003/0011673 A1 * | 1/2003 | Eriksson ................... B23K 9/32 348/42 |
| 2003/0083112 A1 | 5/2003 | Fukuda |
| 2003/0206491 A1 | 11/2003 | Pacheco |
| 2005/0001155 A1 | 1/2005 | Fergason |
| 2005/0005308 A1 | 1/2005 | Logan |
| 2005/0007504 A1 | 1/2005 | Fergason |
| 2006/0203148 A1 | 9/2006 | Magnusson |
| 2007/0056072 A1 | 3/2007 | Steinemann |
| 2007/0056073 A1 | 3/2007 | Martin |
| 2007/0080621 A1 | 4/2007 | Huh |
| 2007/0086508 A1 | 4/2007 | Reading |
| 2008/0120752 A1 | 5/2008 | Huh |
| 2008/0158502 A1 | 7/2008 | Becker |
| 2008/0169277 A1 | 7/2008 | Achtner |
| 2009/0094721 A1 | 4/2009 | Becker |
| 2009/0231423 A1 | 9/2009 | Becker |
| 2009/0276930 A1 | 11/2009 | Becker |
| 2009/0298024 A1 | 12/2009 | Batzler |
| 2010/0062406 A1 | 3/2010 | Zboray |
| 2011/0083241 A1 | 4/2011 | Cole |
| 2011/0183304 A1 * | 7/2011 | Wallace ................. G09B 19/24 434/234 |
| 2011/0186615 A1 | 8/2011 | Gatlin |
| 2013/0206741 A1 * | 8/2013 | Pfeifer ................... B23K 9/095 219/130.01 |
| 2013/0291271 A1 | 11/2013 | Becker |
| 2014/0007312 A1 | 1/2014 | Wright |
| 2014/0346158 A1 * | 11/2014 | Matthews ............ B23K 9/0953 219/130.01 |
| 2015/0056584 A1 * | 2/2015 | Boulware .............. B23K 9/173 434/234 |
| 2015/0234189 A1 | 8/2015 | Lyons |
| 2016/0107258 A1 * | 4/2016 | Denis ..................... A61F 9/067 219/132 |
| 2016/0125653 A1 * | 5/2016 | Denis ..................... B23K 9/322 348/90 |

FOREIGN PATENT DOCUMENTS

| | | |
|---|---|---|
| EP | 0335056 | 10/1989 |
| EP | 0963744 | 12/1999 |
| EP | 1025946 | 8/2000 |
| WO | 0061044 | 10/2000 |
| WO | 0158399 A1 | 8/2001 |
| WO | 2005102230 A1 | 11/2005 |
| WO | 2014188244 | 11/2014 |

OTHER PUBLICATIONS

Fast et al., Virtual Training for Welding, Proceedings of the Third IEEE and ACM International Symposium on Mixed and Augmented Reality (ISMAR 2004); 0-7695-2191-6/04; 2004.
International Search Report from PCT application No. PCT/US2015/053903, dated Dec. 21, 2015, 15 pgs.
Hillers, et al., "TEREBES: Welding helmet with AR capabilites," Proceedings/Virtual and Augmented Reality Status Conference,

(56) References Cited

OTHER PUBLICATIONS

2004 [Leipzig, Feb. 19-20, 2004]/Federal Ministy of Education and Research.

* cited by examiner

STEREOSCOPIC HELMET DISPLAY

BACKGROUND

The invention relates generally to welding systems and, more particularly, to sensing systems for displaying and changing power supply settings remotely.

Welding is a process that has become ubiquitous in various industries for a variety of types of applications. For example, welding is often performed in applications such as shipbuilding, aircraft repair, construction, and so forth. The welding systems often include power supplies that may generate power for consumption during the welding process. However, these power supplies may often be remote from a work area, thereby causing delays if a user changes settings of a power supply due to travel to and from the power supply to make the changes.

BRIEF DESCRIPTION

In a first embodiment, a welding-type system includes a helmet having a first image capture device configured to capture a first set of images of a work area from a first perspective and a second image capture device configured to capture a second set of images of the work area from a second perspective. The helmet also includes an electronic display configured to display the first and second sets of images substantially simultaneously to cause a stereoscopic appearance of the work area via the electronic display. Moreover, the helmet includes an audible command translation unit configured to receive audible commands configured to adjust operation of a power supply configured to supply power for the welding-type system. Furthermore, the welding-type system includes a processing system communicatively coupled to the audible command translation unit and configured to adjust at least one parameter of the power supply based at least in part on the received audible commands.

In another embodiment, a method includes capturing a first image via a first image capture device of a helmet when the first image has a first perspective of a work area. The method also includes capturing a second image via a second image capture device of the helmet when the second image has a second perspective of the work area. Moreover, the method includes displaying the first and second images substantially simultaneously as a stereoscopic image of the work area. Furthermore, the method includes receiving an audible command via an audible command unit of the helmet and adjusting a parameter of a welding-type power supply, at the welding-type power supply, based at least in part on the received audible command.

In a further embodiment, a welding-type system includes a helmet. The helmet includes a first image capture device configured to capture a first image of a work area from a first perspective and a second image capture device configured to capture a second image of the work area from a second perspective. The helmet also includes a first electronic display configured to display the first image to a first portion of the helmet and a second electronic display configure to display the second image to a second portion of the helmet substantially simultaneously to the display of the first image. Moreover, the helmet includes an audible command translation unit configured to receive audible commands configured to adjust operation of a power supply configured to supply power for the welding-type system. Furthermore, the welding-type system include a processing system communicatively coupled to audible command translation unit and configured to adjust at least one parameter of the power supply based at least in part on the received audible commands.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail below, provided herein are systems and methods for viewing and controlling power sources remotely. By viewing and controlling the power sources remotely, an operator may weld a workpiece with desired parameters without walking away from the workpiece. In other embodiments, a welding operator may control the parameters of a weld without spending valuable weld time traveling to the power supply to view and control the power supply. Thus, the operator may weld more quickly and efficiently with desired parameters. Furthermore, the operator may confirm welding parameters prior to a weld without substantial delay that may be required when having to walk back to the power source to change welding parameters.

Figure 1:
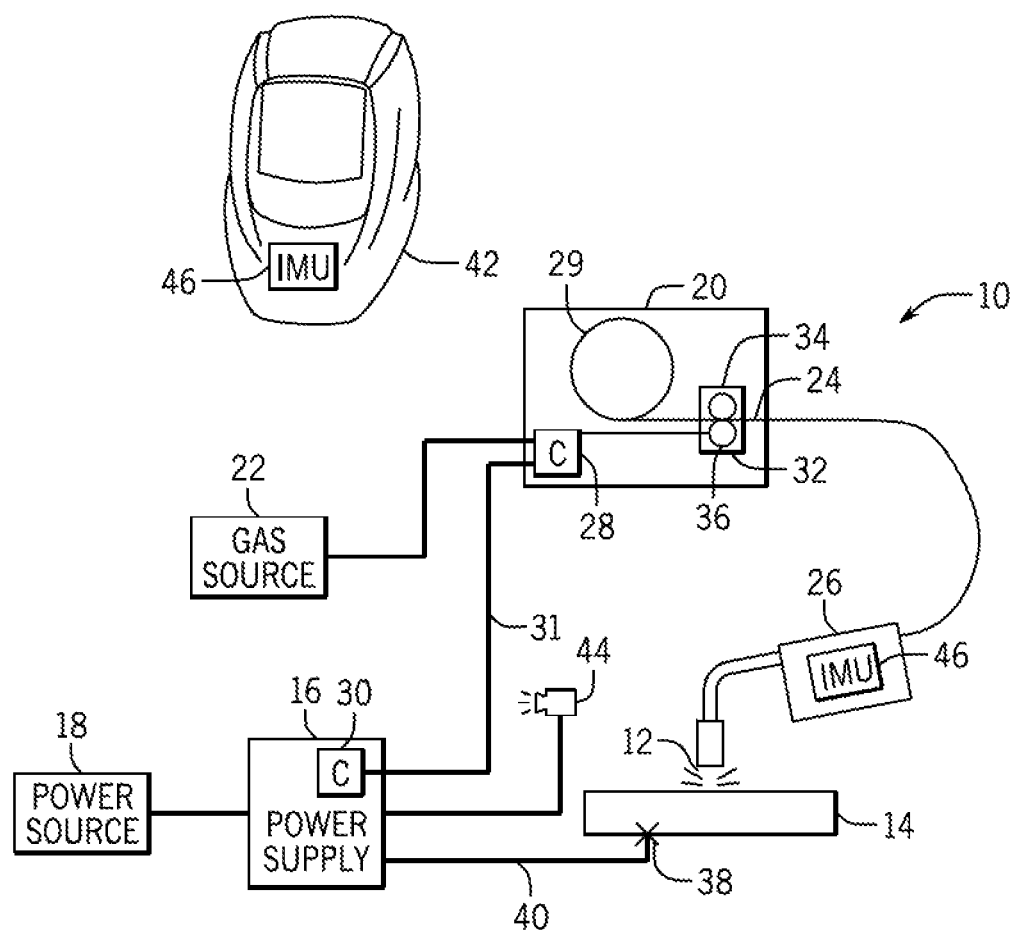
FIG. 1 is a block diagram of an embodiment of a welding system utilizing a welding helmet.

Turning now to the figures, FIG. 1 is a block diagram of an embodiment of a welding system 10 in accordance with the present techniques. The welding system 10 is designed to produce a welding arc 12 with a workpiece 14 (e.g., pipe). The welding arc 12 may be generated by any type of welding system or process, and may be oriented in any desired manner. For example, such welding systems may include gas metal arc welding (GMAW) systems, and may utilize various programmed waveforms and settings. The welding system 10 includes a power supply 16 that will typically be coupled to a power source 18, such as a power grid, an engine, or a combination thereof (e.g., hybrid power). Other power sources may, of course, be utilized including generators and so forth. In the illustrated embodiment, a wire feeder 20 is coupled to a gas source 22 and the power supply 16, and supplies welding wire 24 to a welding torch 26. The welding torch 26 is configured to generate the welding arc 12 between the welding torch 26 and the workpiece 14. The welding wire 24 is fed through the welding torch 26 to the welding arc 12, melted by the welding arc 12, and deposited on the workpiece 14.

The wire feeder 20 will typically include wire feeder control circuitry 28, which regulates the feed of the welding wire 24 from a spool 29 and also may command the output of the power supply 16, among other things. Similarly, the power supply 16 may include power supply control circuitry 30 for monitoring and controlling certain welding parameters and arc-starting parameters. In certain embodiments, the wire feeder control circuitry 28 or the power supply control circuitry 30 may include software, hardware, or a combination thereof. For example, in certain embodiments, the wire feeder control circuitry 28 and/or the power supply control circuitry 30 may include a processor and a tangible, non-transitory, computer-readable memory configured to store instructions to be executed by the processor. In some embodiments, the wire feeder control circuitry 28 may communicate with the power supply control circuitry 30 through a weld cable 31 that is also used to provide power to the wire feeder 20. In some embodiments, the power supply control circuitry 30 may be enclosed in a housing of the power supply 16. In some embodiments, at least some of the processing may be performed by another processor (e.g., processor in the helmet).

The spool 29 of the wire feeder 20 will contain a length of welding wire 24 that is consumed during the welding operation. The welding wire 24 is advanced by a wire drive assembly 32, typically through the use of an electric motor used to drive wheels 34 and 36 used to advance the welding wire 24. In some embodiments, the electric motor is under control of the control circuitry 28. In addition, the workpiece 14 may be coupled to the power supply 16 by a clamp 38 connected to a work cable 40 to complete an electrical circuit when the welding arc 12 is established between the welding torch 26 and the workpiece 14.

Placement of the welding torch 26 at a location proximate to the workpiece 14 allows electrical current, which is provided by the power supply 16 and routed to the welding torch 26, to arc from the welding torch 26 to the workpiece 14. As described above, this arcing completes an electrical circuit that includes the power supply 16, the welding torch 26, the workpiece 14, and the work cable 40. Particularly, in operation, electrical current passes from the power supply 16, to the welding torch 26, to the workpiece 14, which is typically connected back to the power supply 16 via the work cable 40. The arc generates a relatively large amount of heat that causes part of the workpiece 14 and the filler metal of the welding wire 24 to transition to a molten state that fuses the materials, forming the weld.

In certain embodiments, to shield the weld area from being oxidized or contaminated during welding, to enhance arc performance, and to improve the resulting weld, the welding system 10 may also feed an inert shielding gas to the welding torch 26 from the gas source 22. It is worth noting, however, that a variety of shielding materials for protecting the weld location may be employed in addition to, or in place of, the inert shielding gas, including active gases and particulate solids. Moreover, in other welding processes, such gases may not be used, while the techniques disclosed herein are equally applicable.

Although FIG. 1 illustrates a GMAW system, the presently disclosed techniques may be similarly applied across other types of welding systems, including gas tungsten arc welding (GTAW) systems and shielded metal arc welding (SMAW) systems, among others. Accordingly, embodiments of the sensor-based power supply controls may be utilized with welding systems that include the wire feeder 20 and gas source 22 or with systems that do not include a wire feeder 20 and/or a gas source 22 (e.g., embodiments where the welding torch 26 is directly coupled to the power supply 16), depending on implementation-specific considerations.

Presently disclosed embodiments are directed to remote power supply monitoring, viewing, and control. In some embodiments, data related to the power supply 16 may be sent to a welding helmet 42 and presented to an operator wearing the helmet 42. In some embodiments, the data may be presented visually or audibly to the operator. Furthermore, visual data may include images of the power supply 16 taken by one or more cameras 44 showing settings of the power supply 16. In certain embodiments, the operator may modify parameters remotely based on the presented parameters. For example, in certain embodiments, the operator may speak audible commands into the helmet 42 or issue commands that are detected by the helmet 42 or an inertial measurement unit (IMU) 46 in the welding torch 26, the helmet 42, gloves, and/or other suitable locations. In some embodiments, the commands may be detected via a camera and other sensory apparatus in a work area where welding is being performed. Additionally or alternatively, some commands may be received via an electronic device, such as a computer, smart phone, tablet, or other electronic device capable of receiving input from the operator.

In certain embodiments, the IMU 46 may include an accelerometer, a magnetometer, a rate sensor (e.g., a gyroscope sensor), sensor, or other sensors capable of measuring movements of the operator. As used herein, a rate sensor may include MEMs based sensors or any device which provides a signal output indicating an angular rate of change within a three dimensional frame of reference. For example, a single axis rate sensor would indicate a rate of change about a single coordinate normal to the sensor's reference plane. The accelerometer may include a single triaxial accelerometer capable of measuring dynamic motion, such as weld weaving. In other embodiments, the accelerometer may include one or more orientation sensors to determine a change of welding torch 26 orientations in one or more dimensions. For example, a two-dimensional position may be calculated with respect to a plane parallel to a direction of gravity based on two accelerometers. In some embodiments, the rate sensor may include one or more rate sensors, such as a single triaxial rate sensor. The power supply control circuitry 30 and/or the wire feeder control circuitry 28 may use the rate sensor to supplement data from the accelerometer to measure smaller or finer movements. In certain embodiments, the magnetometer may include one or more magnetometer sensors, such as a single triaxial magnetometer. The power supply control circuitry 30 and/or the wire feeder control circuitry 28 may use the magnetometer to determine changes in magnetic fields such as movement of the welding torch 26 or other objects in the weld area. Using one or more sensor types in the IMU 46, the welding system 10, via the control circuitry 30 and/or the wire feeder control circuitry 28, may receive detected motion data that may control the power supply 16.

Figure 2:
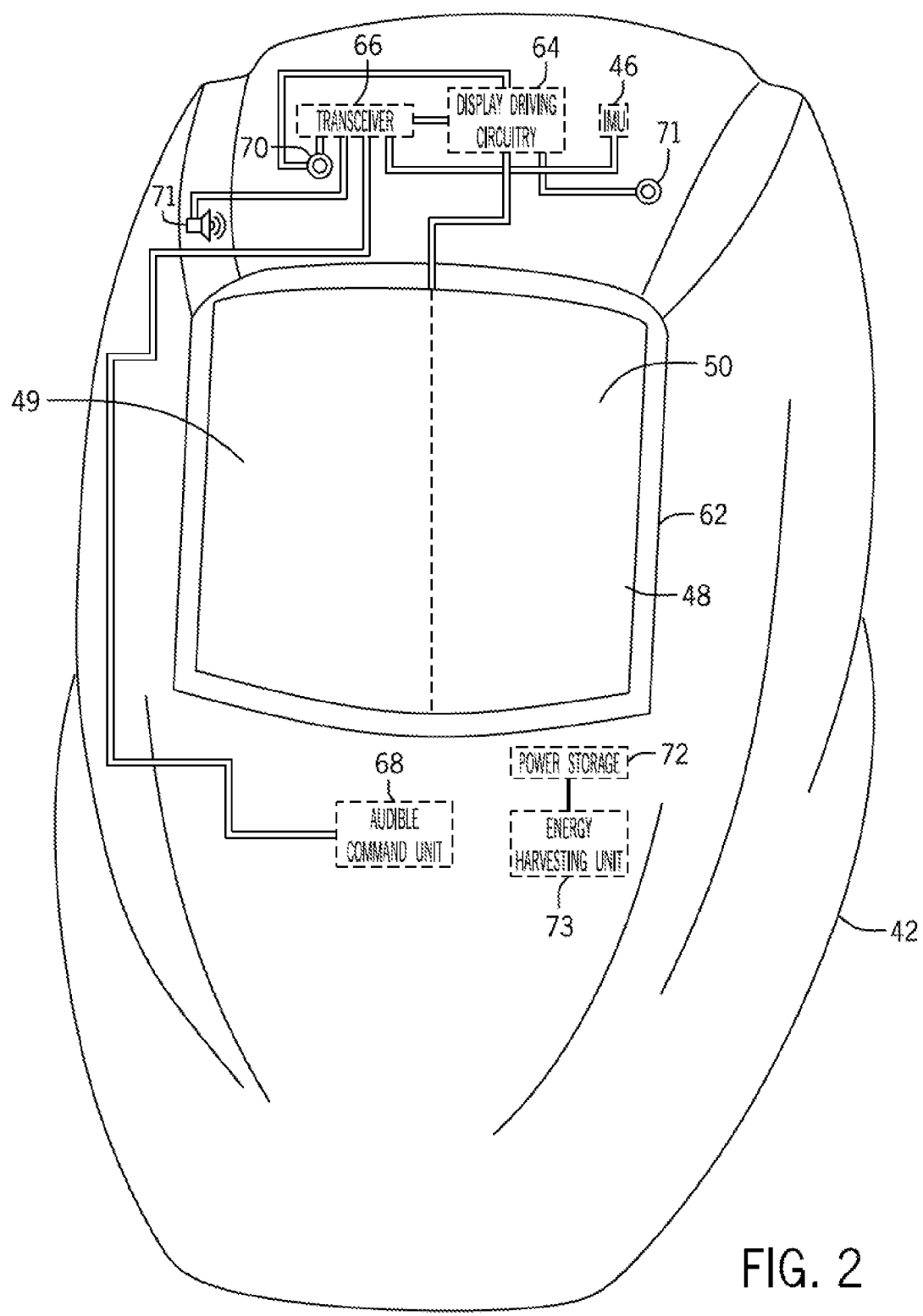
FIG. 2 is a block diagram of an embodiment of the welding helmet of FIG. 1 illustrating an electronic display.

Using data from one or more of the sensors, the power supply control circuitry 30 and/or the wire feeder control circuitry 28 may control the power supply 16 to change one or more parameters as desired by an operator without the operator physically walking to the power supply 16. As previously discussed, the welding helmet 42 may display the parameters to be controlled, the power supply 16, or a representation of the power supply 16 via a display, such as the display 48 included inside the welding helmet 42 of FIG. 2. In certain embodiments, the display 48 may include an electronic screen used to replace a viewing area of traditional welding helmets. For example, in some embodiments, auto-darkening glass of a welding helmet may be removed and replaced with the display 48. In some embodiments, the display 48 may be split into two regions (e.g., regions 49 and 50) that each display different views from different cameras. In other words, a first camera may capture a first perspective (e.g., right eye perspective) that is displayed in the region 49, and a second camera may capture a second perspective (e.g., left eye perspective). In certain embodiments, the display 48 may include two separate displays (e.g., each displays images from the right and left eye perspectives corresponding to regions 49 and 50), each display capable of showing images independent from the other display. In such embodiments, the two displays may be used to show a stereoscopic view of various objects, such as the work area and/or the power supply 16. In some embodiments, each display may be only visible by one eye of the operator. For example, the helmet 42 may include a baffle that blocks visibility of at least a portion of one of the displays by one eye of the operator.

Figure 3:
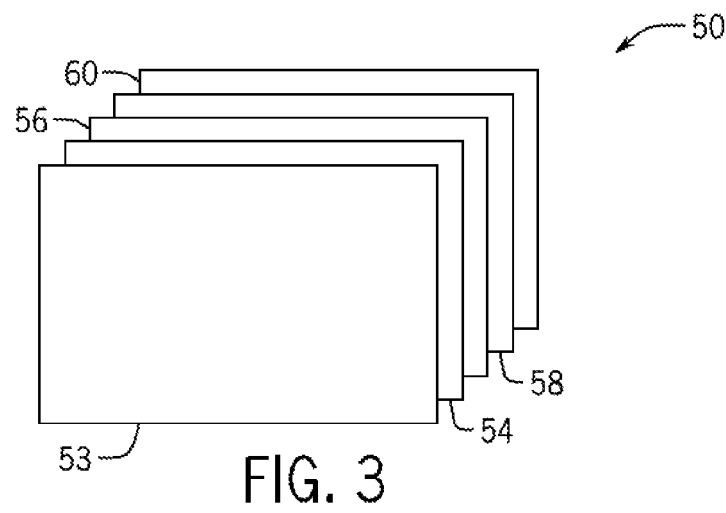
FIG. 3 is an exploded view of an embodiment of layers that may be included in the electronic display of FIG. 2.

In other embodiments, a clear display (or displays) 48 may be layered onto glass of a welding helmet. FIG. 3 illustrates layers 51 of each of the display(s) 48 that may be placed in the viewing area of the helmet 42. Although the layers 51 includes five layers, in some embodiments, additional layers may be included, some layers may be omitted, two or more layers may combined into a single layer, and/or some layers may be separable into multiple distinct layers (e.g., a polarizing layer, transistor layer, etc.). In other words, in some embodiments, the layers 51 may include 1, 2, 3, 4, 5, 6, or more layers. In the illustrated embodiment, the layers 51 include an inner transparent layer 52, a transparent display layer 54, an insulating layer 56, an autodarkening layer 58, and an outer transparent layer 60. The inner transparent layer 52 may protect the display layer 54 from contact and/or damage from contacting objects within the helmet 42 while enabling a user wearing the helmet 42 to see the images shown by the transparent display layer 54. For example, in some embodiments, the inner transparent layer 52 may include glass or a transparent plastic.

The transparent display layer 54 may include display circuitry that enables the user to see images created and intended to be displayed while still observing the user's actual surrounding area through the transparent display circuitry layer 54. For example, the transparent display layer 54 may include a transparent liquid crystal display (LCD), an organic light emitting diode (OLED) display, or other displays that enable an operator to see what is on the display layer 54 while still being able to see through the display layer 54. In some embodiments, the transparent display layer 54 may include a prism that reflects images projected to one or more parts of the prism. As discussed below, in some embodiments, the display layer 54 may only be capable of displaying images on a portion of the viewing area. However, in some embodiments, the display layer 54 may encompass the whole viewing area of the helmet 42.

In some embodiments, the layers 51 include an insulating layer 56 that separates the display layer 54 from the auto-darkening layer 58 to block interference of operation of electronic components of the display layer 54 and/or the autodarkening layer 58 from other layers or each other. In some embodiments, the insulating layer 56 may include a substrate layer of the transparent display layer 54. The autodarkening layer 58 may include electrochromic, photochromic, thermochromic, suspended particle, micro-blind, or other autodarkening smart glass. In some embodiments, the display layer 54 and the autodarkening layers 58 may be combined into a single layer. For example, the liquid crystals of a transparent LCD may be used to darken incoming light by partially closing and/or displaying images using color filters on at least some of the liquid crystals. In some embodiments, the layers 51 may also include an outer transparent layer 60 that at least protects the other layers of the layers 51 from damage outside the helmet 42.

Returning to FIG. 2, in some embodiments, the display 48 may be coupled to the helmet 42 via a bevel 62 that houses display circuitry and couples the display 48 to display driving circuitry 64. In some embodiments, the display driving circuitry 64 may include row and column pixel controls for the display layer 54 or a projection device for projecting images onto a prism of the display layer 54. The helmet 42 may also include a transceiver 66 that receives image data from one or more remote devices (e.g., camera 44) and returns information to the remote device. In certain embodiments, the transceiver 66 may include a wireless transceiver, such as a ZigBee, 802.15.4, Bluetooth, 802.11, and/or other wireless transceiver. Additionally or alternatively, the transceiver 66 may include a wired connection transceiver. In some embodiments, the transceiver 66 may be a uni-direction receiver that receives video data. However, in some embodiments, the transceiver 66 may send commands from the helmet 42 back to a control unit, such as the power supply control circuitry 30 and/or the wire feeder control circuitry 28. For example, the transceiver 66 may send motion commands detected by the IMU 46, auditory commands (e.g., vocal commands) detected by an audible command unit 68, and/or visual commands detected by camera(s) 70 and/or 71. In some embodiments, at least in some modes, the transceiver 66 may not receive images for display via the display 42 because the display 42 displays images captured from the camera(s) 70 and/or 71, rather than receiving images from a remote location.

In some embodiments, the helmet 42 may include a speaker 72 used to convey auditory information to the user. For example, the speaker 72 may receive audible signals from the power supply control circuitry 30 and/or the wire feeder control circuitry 28 via the transceiver 66 indicating a power supply parameter, receipt of a command from the user, a type of power supply 16, or other information useful in informing a user of changes to operating parameters and generate an audible indication of such information to the user.

The helmet 42 may also include a power storage 73 that stores power for use by the transceiver 66, display 48, display driving circuitry 64, IMU 46, display 48, speaker 72, audible command unit 68, and/or additional circuitry. The power storage 73 may include any suitable unit for storing power that may be used to power electrical components, such as capacitors or batteries formed from galvanic cells, electrolytic cells, fuel cells, flow cells, and/or voltaic piles. The power storage 73 may store energy received from an energy harvesting unit 74 and/or external power source (e.g., AC line power). The energy harvesting unit 74 derives energy from around the user to provide power to the power storage 73. For example, the energy harvesting unit 74 may include kinetic energy captures using electromagnetic generators, photovoltaic cells, thermoelectric generators, antennas to recover radio wave energy, or other items capable of converting energy into a form (e.g., chemical or electrical) suitable for storage in the power storage 73. For example, the energy harvesting unit 74 may include a solar panel that absorb UV light from the welding torch 26 and generates power for storage in the power storage 73. In some embodiments, the energy harvesting unit 74 may use Maximum Power Point Tracking (MPPT) technique to use to get enhanced power from one or more photovoltaic devices, (e.g., solar panels). In other words, the energy harvesting unit 71 and/or the power storage 73 may employ MPPT to achieve enhanced power production from the energy harvesting unit 74 by modeling the power generation based on the power generation relationship to UV irradiation, temperature, and total resistance by sampling an I-V curve from the energy harvesting unit 74 to apply proper resistance to enhance power generation. Specifically, the MPP is the product of the MPP voltage and the MPP current.

Figure 4:
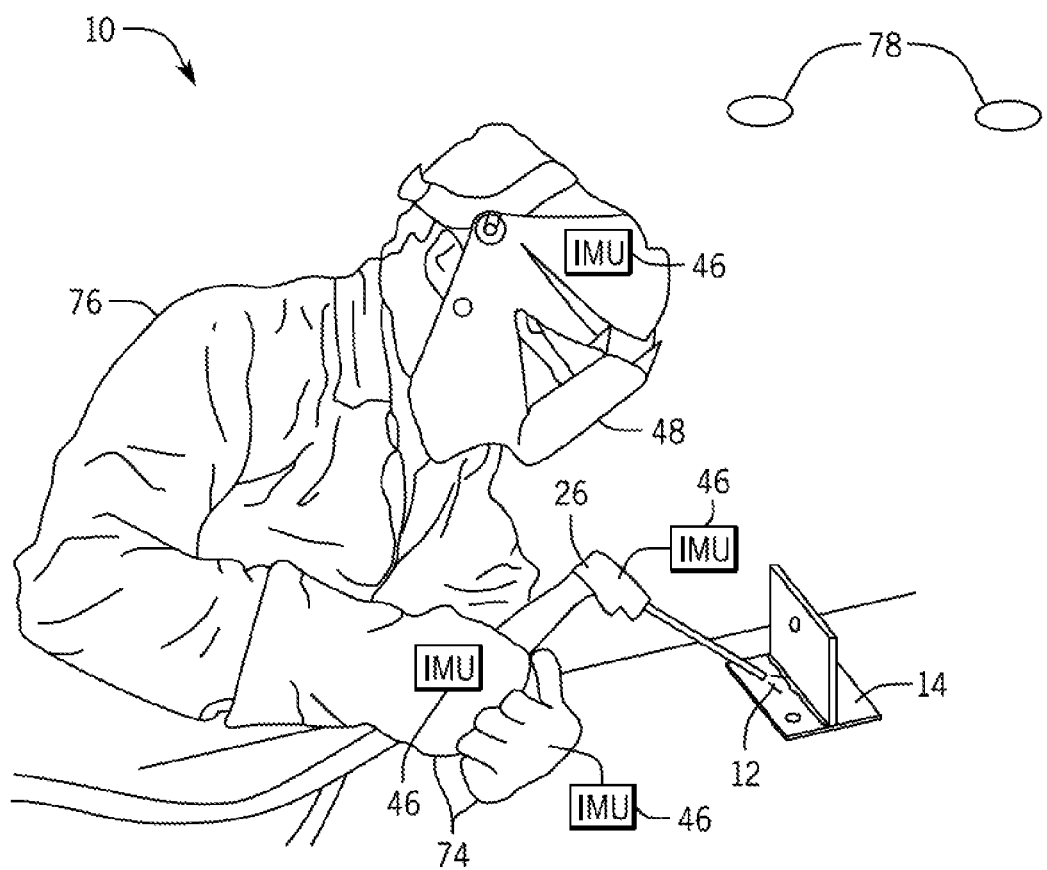
FIG. 4 is a perspective view of an embodiment of the welding system of FIG. 1 showing an inertial measurement unit.

FIG. 4 is a perspective view of an embodiment of the welding system 10 capable of monitoring a position of the welding helmet 42, welding torch 26, and/or gloves 75 to detect control commands from an operator. In the depicted welding system 10, an operator 76 is wearing the welding helmet 42 while welding. In certain embodiments, external helmet position detection sensors 78 are located near the operator 76 in a welding job area to aid the data from the IMUs 46 in assessing the position and orientation of the welding helmet 42, welding torch 26, and/or gloves 75.

It should be noted that the sensors 78 may include, or be replaced by, any method or device capable of detecting the position of the welding helmet 42. For example, the sensors 78 may include a stereo-vision camera or one or more mono-vision cameras located overhead to determine the location and orientation of the welding helmet 42. The cameras may be located on the welding helmet 42 (e.g., cameras 70 and/or 71) to locate the relative position of the helmet 42, welding torch 26, gloves 75, and/or capturing images of the work area for display via the display 48. The sensors 78 may include optical sensors for determining the position of the welding helmet 42, welding torch 26, and/or gloves 75 by determining a position of a predefined point, such as the workpiece 14. In some embodiments, the helmet 42 may include markings that reflect light or active visual markings that include infrared LEDs. In certain embodiments, the orientation of the helmet 42, welding torch 26, and/or gloves 75 in relation to each other, in relation to the workpiece 14, or in relation to the operator may be visually determined, for example, via helmet markings or geometric features detected by a plurality of camera imagers external to the welding helmet 42.

In still other embodiments, the sensors 78 may include a single optical sensor configured to detect structured light projected onto the welding helmet 42 from a light source external to the welding helmet 42. The light source may include a point source at a fixed location relative to the sensors 78. The light source may project a grid or other structured pattern toward the helmet 42, welding torch 26, and/or gloves 75. Wherever the pattern strikes the welding helmet 42 (or welding torch 26 or gloves 75), the light may produce a pattern indicative of the shape and distance of the welding helmet 42 (or welding torch 26 of gloves 75) from the sensors 78. As the light hits the welding helmet 42 (or welding torch 26 of gloves 75) from different angles, the projected grid may become distorted based on the contours of the welding helmet 42 (or welding torch 26 of gloves 75). The welding helmet 42 (or welding torch 26 of gloves 75) may be shaped such that the distorted grid may be utilized to identify a position, distance, and orientation of the welding helmet 42 (or welding torch 26 of gloves 75) via image processing of images acquired via the sensors 78. The structured light could include an array of points, circles, stripes, or any desirable collection of light patterns that can be recognizable.

Figure 5:
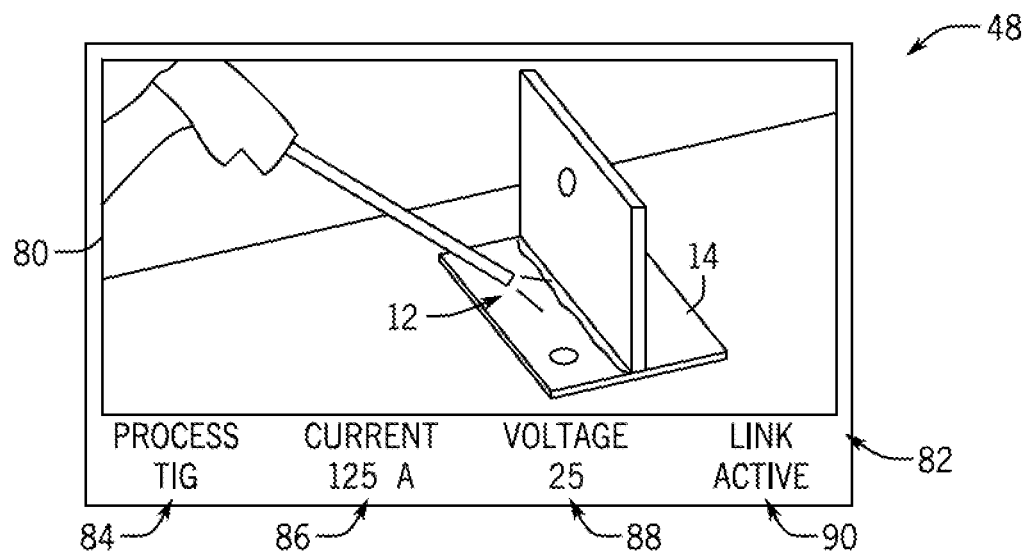
FIG. 5 is an embodiment of an image of a working view that may be displayed by the display of FIG. 2.

As previously discussed, the helmet 42 may display various parameters of the power supply 16. For example, FIG. 5 illustrates an image that might be presented to the user via the display 48 (e.g., in region 49 and/or 50). The helmet 42 may enable the user to view a workpiece 14 and a welding arc 12. As previously discussed, in some embodiments, the display 48 reproduces a working view 80 via image capturing (e.g., via one or more cameras 70 and/or 71). In certain embodiments, the display 48 may be at least partially transparent to enable the user to view the working view 80. In other embodiments, the display 48 may display captured images of the working view 80 via the camera(s) 70 and/or 71. In some embodiments, the display 48 may be horizontally bifurcated into two separate displays or may be horizontally partitioned into two viewing areas that enable the helmet 42 to present different images to each eye of the welder. For example, the left display or display area may be used to present an image stream from a left-side camera that a captures a perspective similar to that which would be viewed by a left eye. Similarly, the right display or display area may be used to present an image stream from a right-side camera that captures a perspective similar to that which would be viewed by a right eye. This stereoscopic viewing would allow the welder to see the working area more accurately to add depth perception and three-dimensional viewing to the display 48.

In some embodiments, the display 48 may display an autostereogram. An autostereogram is a single-image stereogram (SIS) that includes small pixels such as neighboring vertical slices of an image that matches patterns to generating a virtual depth perception. For example, images may be sliced into a number of strips (e.g., 8). The resulting image combination of the images may allow a user to view a virtual 3D image by slightly defocusing their eyes (e.g., focusing in front of or behind the image).

In certain embodiments, the display 48 may include a heads up display (HUD) 82 that informs the user of various parameters of the power supply 16 and/or the welding process being used. For example, the HUD 82 may include a process type indication 84, a current level indication 86, a voltage level indication 88, and a link indication 90, and/or other parameters that may be helpful for the operator to know for the welding process. The process type indication 84 indicates what type of welding process is currently being employed, such as tungsten inert gas (TIG) welding, metallic inert gas (MIG) welding, shielded metal arc welding (SMAW), gas metal arc welding (GMAW), or other suitable welding processes. The current level indication 86 indicates a current level for the welding process. Similarly, the voltage level indication 88 indicates a voltage level for the welding process. Furthermore, the link indication 90 indicates that a connection to the power supply 16 from the welding torch 26 is active or inactive. In some embodiments, the link indication 90 indicates that the HUD 82 is actively receiving data from the power supply 16 and that the currently displayed parameters are recently received from the power supply 16.

Figure 6:
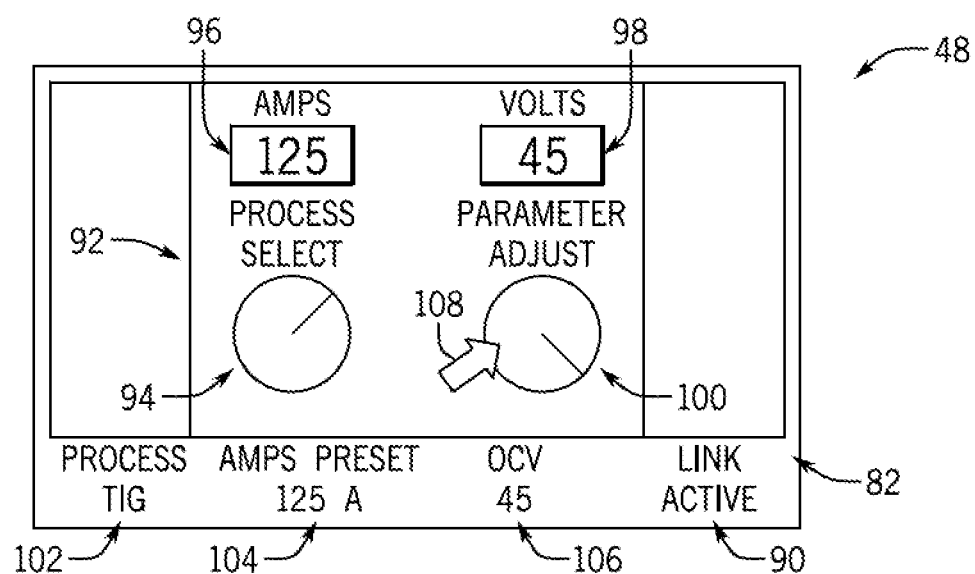
FIG. 6 is an embodiment of an image of a parameter adjustment view that may be displayed by the display of FIG. 2.

In some embodiments, while viewing the working view 80, the operator may initiate a power supply view in which the display 48 (e.g., in region 49 and/or 50) shows a power supply 92, such as the display 48 illustrated in FIG. 6. In some embodiments, the power supply 92 may be a caricature or simplified view corresponding to a type matching the type of power supply 16. In some embodiments, the power supply 92 may be an image of the actual power supply 16 either previously saved or shown in substantially real time via the camera 44. In certain embodiments, the power supply 92 may include various information and manipulatables that may be found on the front of the power supply 16. For example, the power supply 92 may include a process selection dial 94, a current unit 96, a voltage unit 98, and a parameter adjust dial 100. The process selection dial 94 may be used to set what type of process is used for the weld process and indicated by the process indicator 102 of the HUD 82. Similarly, the current unit 96 may display a current level that may also be reflected in the current level indicator 104 of the HUD 82, and the voltage unit 98 may display a voltage level that may also be reflected in the voltage level indicator 106 of the HUD 82.

In the present embodiment, the voltage level indicator 106 indicates an open circuit voltage (OCV) that corresponds to a difference in electrical potential between two terminals of the power supply 16 when disconnected from an external circuit (e.g., circuit including the welding torch 26 and the workpiece 14). In some embodiments, the parameter adjust dial 100 may be used to adjust voltage, current, or other parameters of the power supply 16. Although the process selection dial 94 and the parameter adjust dial 100 are dials, in some embodiments, the dials 94, 100 may be replaced by any other manipulatable capable of receiving user input, such as arrows, number entry keyboards, and so forth. In some embodiments, the operator may manipulate one or more parameters using a cursor 108.

In certain embodiments, the cursor may be a box or other indicator that indicates which parameter is being changed. In some embodiments, the cursor may be moved using gestures (e.g., head movements up or down, head movements left or right, hand gestures up or down, hand gestures left or right) or vocal commands (e.g., "left"). In some embodiments, the hand gestures may include a horizontal swipe (e.g., left or right), a vertical swipe (e.g., up or down), a circular motion (e.g., clockwise or counterclockwise loop), a twist (e.g., clockwise or counterclockwise rotation of the torch 26), or other gestures that may be recognized by the sensors. In other words, the raw data generated by the sensors may be analyzed to determine when certain gestures are being performed by the operator. In some embodiments, the gestures may be analyzed by a preprocessor prior to communication to the power supply control circuitry 30 and/or the wire feeder control circuitry 28. In other embodiments, the power supply control circuitry 30 and/or the wire feeder control circuitry 28 may analyze raw data from the sensors to recognize the gestures. In some embodiments, the cursor 108 and manipulatables may be replaced with vocal commands (e.g., "amplitude increase by 5").

In some embodiments, the process selection dial 94 and/or the parameter adjust dial 100 may be omitted or collapsed with respective display portions. For example, functionality of the process selection dial 94 may be included into the process indicator 102. In some embodiments, the display portions (e.g., portions of the HUD 82) may be only manipulatable in one mode while locked in another mode. For example, a user may issue a voice command, such as "parameter adjustment mode," that initiates the parameter adjustment mode that allows the operator to modify power supply parameters remotely.

Although the foregoing discussion contemplates displaying power supply monitoring and manipulation via the welding helmet 42, in some embodiments, at least some of the display and or control of the power supply 16 may be performed via a smart device (e.g., a smart phone). For example, when a smart device is on the same network (e.g., WiFi) as the power supply 16, a control application may be employed to monitor and change parameters of the power supply 16.

Figure 7:
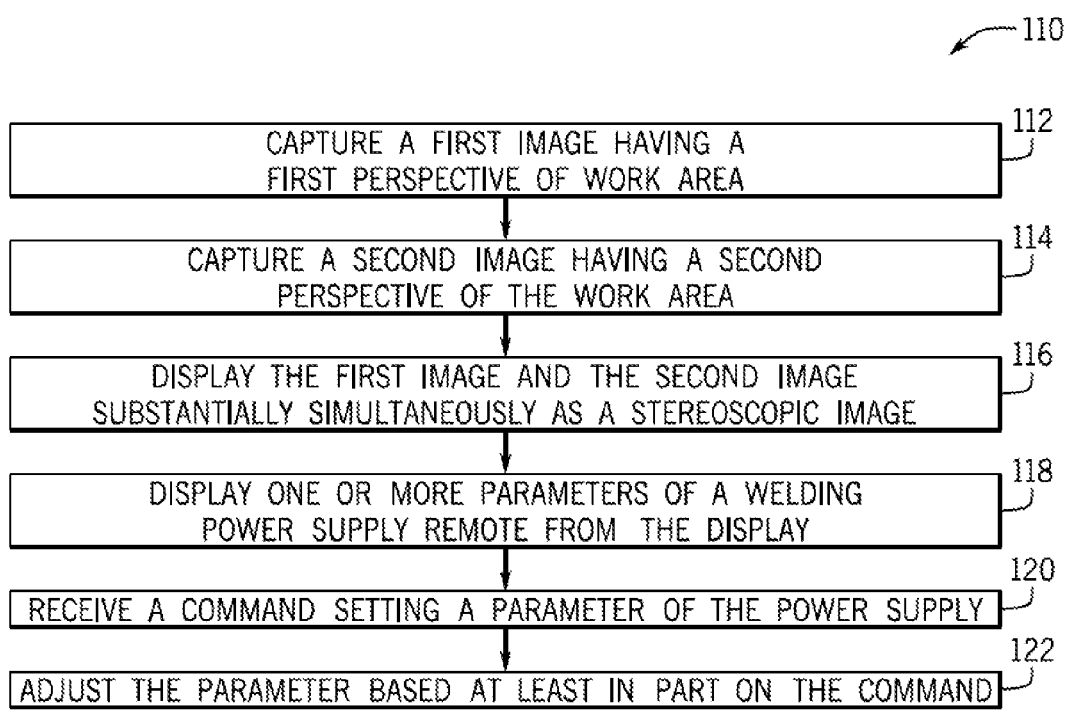
FIG. 7 is a flowchart diagram view of an embodiment of a process for adjusting parameters of the power supply of the welding system of FIG. 1.

FIG. 7 illustrates a process 110 that may be used to monitor and/or change parameters of the power supply 16 remotely. The process 110 includes capturing a first image having a first perspective of a work area (block 112). For example, the first perspective may include a perspective that may be viewed by the right eye and captured by a camera (e.g., camera 70) that is near a location of the right eye. The process 110 also includes capturing a second image having a second perspective of the work area (e.g., camera 71). The display(s) 48 (e.g., regions 49 and/or 50) then display the first and second images substantially simultaneously (block 116). For example, the left and right perspectives may be displayed simultaneously or alternatively at a fast rate that causes the perspectives appear to be displayed simultaneously. In some embodiments, each perspective may be displayed on the entire display(s) 48 and filtered to the left and right eyes of a user using a shutter or other method that blocks viewing of the display perspective to the wrong eye. Moreover, the first image and the second image may belong to sets of images. In some embodiments, the first and second sets of images may be interwoven such that the display alternatively displays images from the first and second perspectives.

The process 110 also includes displaying, via a smart device or a welding helmet, one or more parameters of a power supply 16 to a user remote from the power supply 16 (block 118). In some embodiments, the display may be presented differently in different regions and/or displays to give the representation of the power supply 16 a pseudo-stereoscopic view. The process 110 also includes receiving commands from a user remote from a power supply 16 (block 120). For example, the commands may include gestures and/or audio commands from a user that is far away from a power supply 16 without direct sight of the power supply 16. Based on the commands, at least one parameter of the power supply 16 may be adjusted (block 122).

For instance, in certain embodiments, when a welding operator is in the middle of a weld, the operator's welding helmet 42 may display a HUD 82 showing parameters of the power supply 16. For at least a portion of the weld, the operator may desire to change the current. Accordingly, the operator may say "parameter adjust mode" or press a button on the welding helmet 42. The display 48 may switch from a working view to show a caricature of the power supply 16. Although the operator may use hand, head, and/or body gestures to select and modify parameters, the operator may be currently welding and may not want to disturb the arc 12. For example, for certain welds or certain types of welds (e.g., TIG vs. MIG), more sensitivity may be desired. As such, the operator may say "amps up by five" into a microphone in the welding helmet 42. The welding helmet 42 sends the command—either as raw audio, processed audio, or a digital representation of the command—to a control device, such as the power supply control circuitry 30. Once the control device receives the command as either a vocal command or gesture, the control device increases the current of the power supply 16.

Although the foregoing discussion relates generally to displaying power supply information, in some embodiments, other information may be displayed by the display 48 either as additional information or as alternative information. Specifically, the IMUs 46 or other sensors may determine parameters about the weld joint and/or process that may be indicative of a quality of the weld joint. For example, the IMUs 46 may be used to determine travel speed of the welding torch 26. This information may be displayed to the user via the display 48. Additionally or alternatively, welding instructions based on the determined parameters may be provided to the user via the display 48. For example, the display 48 may show an up arrow asking that the user increase speed, current, or voltage of the weld. Additionally or alternatively, the display 48 may instruct the user to modify orientation of the welding torch 26 in relation to the welding helmet 42 and/or workpiece 14.

Although the foregoing discussion generally relates to welding torches, in some embodiments, motion sensing may be used for any welding-type tool or accessory associated with a welding-type process. As used herein, welding-type refers to any process related to welding, such as welding, cutting, or gouging. Furthermore, a welding-type tool or accessory may be any tool or accessory using in such processes. For example, welding-type tools may include torches, electrode holders, machining tools, or other similar tools that may be used in the welding-type processes. Moreover, welding-type accessories may include wearable devices, such as a helmet, a jacket, a glove, a bracelet, or other devices that may be worn by an operator.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A welding-type system, comprising:
a helmet comprising:
    a first image capture device configured to capture a first set of images of a work area from a first perspective during a welding operation;
    a second image capture device configured to capture a second set of images of the work area from a second perspective during the welding operation;
    an electronic display configured to display the first and second sets of images substantially simultaneously to cause a stereoscopic appearance of the work area depicting the welding operation via the electronic display during the welding operation; and
a processing system communicatively coupled to the helmet and configured to adjust at least one parameter of a power supply based at least in part on feedback received from the helmet and
an energy harvesting unit that captures light from the welding operation and converts the light into energy that is used in displaying the first and second sets of images.

2. The welding-type system of claim 1, wherein the helmet comprises an inertial measurement unit configured to detect movement of the helmet, and the processing system is configured to adjust at least one parameter of the power supply based at least in part on the detected movement of the helmet.

3. The welding-type system of claim 1, comprising a welding-type tool communicatively coupled to the power supply, wherein the welding-type tool comprises an inertial measurement unit configured to detect movement of the welding-type tool, wherein the processing system is configured to adjust one or more parameters of the power supply based at least in part on the movement of the welding-type tool.

4. The welding-type system of claim 1, comprising a wearable device comprising an inertial measurement unit configured to detect movement of the wearable device, wherein the processing system is configured to adjust one or more parameters of the power supply based at least in part on the detected movement of the wearable device.

5. The welding-type system of claim 1, wherein the electronic display is configured to display a representation of the power supply and to display the at least one parameter of the power supply.

6. The welding-type system of claim 1, wherein the at least one parameter comprises a current level of the power supply, a voltage level of the power supply, or a type of a welding-type process powered by the power supply.

7. The welding-type system of claim 1, wherein displaying the first and second sets of images substantially simultaneously comprises alternating between the first and second sets of images at a rate faster than noticeable by an operator's eyes.

8. The welding-type system of claim 1, wherein the processing system comprises power supply control circuitry.

9. The welding-type system of claim 1, comprising a transceiver configured to transmit information indicative of audible commands to the power supply or a transmitter configured to transmit information indicative of the audible commands to the power supply.

10. The welding-type system of claim 1, wherein the electronic display comprises a transparent light emitting diode display, a transparent liquid crystal displays, or a transparent organic light emitting diode display.

11. The welding-type system of claim 1, wherein the first image capture device comprises a camera configured to capture images of the first perspective of the work area, wherein the first perspective is approximately a perspective that would be viewed by a right eye of a user wearing the helmet.

12. The welding-type system of claim 11, wherein the second image capture device comprises a camera configured to capture images of the second perspective of the work area, wherein the second perspective is approximately a perspective that would be viewed by a left eye of a user wearing the helmet.

13. The welding-type system of claim 1, wherein the electronic display blocks a direct view of the work area during the welding operation and displays a virtual view using the first and second sets of images.

14. The welding-type system of claim 1, wherein the welding operation comprises utilizing a welding arc.

15. The welding-type system of claim 1, wherein the helmet comprises an audible command translation unit configured to receive audible commands configured to adjust operation of the power supply, and the processing system is configured to adjust at least one parameter of the power supply based at least in part on the received audible commands.

16. A welding-type system, comprising:
a helmet comprising:
    a first image capture device configured to capture a first set of images of a work area from a first perspective during a welding operation;
    a second image capture device configured to capture a second set of images of the work area from a second perspective during the welding operation;
    an electronic display configured to display the first and second sets of images substantially simultaneously to cause a stereoscopic appearance of the work area depicting the welding operation via the electronic display during the welding operation; and
a processing system communicatively coupled to the helmet and configured to adjust at least one parameter of a power supply based at least in part on feedback received from the helmet and an energy harvesting unit that captures kinetic movement of the helmet and converts the kinetic movement into energy that is used in displaying the first and second sets of images.

17. The welding-type system of claim 16, wherein the helmet comprises an inertial measurement unit configured to detect movement of the helmet, and the welding-type system comprises a processing system configured to adjust at least one parameter of the power supply based at least in part on the detected movement of the helmet.

18. The welding-type system of claim 16, comprising a welding-type tool communicatively coupled to the power supply, wherein the welding-type tool comprises an inertial measurement unit configured to detect movement of the welding-type tool, wherein the welding-type system comprises a processing system configured to adjust one or more parameters of the power supply based at least in part on the movement of the welding-type tool.

19. The welding-type system of claim 16, comprising a wearable device comprising an inertial measurement unit configured to detect movement of the wearable device, wherein the welding-type system comprises a processing system configured to adjust one or more parameters of the power supply based at least in part on the detected movement of the wearable device.

20. The welding-type system of claim 16, wherein the electronic display is configured to display a representation of the power supply and to display the at least one parameter of the power supply.

21. The welding-type system of claim 16, wherein the at least one parameter comprises a current level of the power supply, a voltage level of the power supply, or a type of a welding-type process powered by the power supply.

22. The welding-type system of claim 16, wherein displaying the first and second sets of images substantially simultaneously comprises alternating between the first and second sets of images at a rate faster than noticeable by an operator's eyes.

23. The welding-type system of claim 16, wherein the processing system comprises power supply control circuitry.

24. The welding-type system of claim 16, comprising a transceiver configured to transmit information indicative of audible commands to the power supply or a transmitter configured to transmit information indicative of the audible commands to the power supply.

25. The welding-type system of claim 16, wherein the electronic display comprises a transparent light emitting diode display, a transparent liquid crystal displays, or a transparent organic light emitting diode display.

26. The welding-type system of claim 16, wherein the first image capture device comprises a camera configured to capture images of the first perspective of the work area, wherein the first perspective is approximately a perspective that would be viewed by a right eye of a user wearing the helmet.

27. The welding-type system of claim 26, wherein the second image capture device comprises a camera configured to capture images of the second perspective of the work area, wherein the second perspective is approximately a perspective that would be viewed by a left eye of a user wearing the helmet.

28. The welding-type system of claim 16, wherein the electronic display blocks a direct view of the work area during the welding operation and displays a virtual view using the first and second sets of images.

29. The welding-type system of claim 16, wherein the welding operation comprises utilizing a welding arc.

30. The welding-type system of claim 16, wherein the helmet comprises an audible command translation unit configured to receive audible commands configured to adjust operation of the power supply, and the processing system is configured to adjust at least one parameter of the power supply based at least in part on the received audible commands.

* * * * *